US010490051B2

(12) United States Patent
Theytaz et al.

(10) Patent No.: US 10,490,051 B2
(45) Date of Patent: Nov. 26, 2019

(54) METHOD AND SYSTEM FOR DETECTING FATIGUE IN AN ATHLETE

(71) Applicant: Logitech Europe S.A., Lausanne (CH)

(72) Inventors: Olivier Theytaz, Savigny (CH); Daniel Bonanno, Geneva (CH); Jean-Michel Chardon, Vufflens-la-Ville (CH)

(73) Assignee: Logitech Europe S.A., Lausanne (CH)

( * ) Notice: Subject to any disclaimer, the term of this patent is extended or adjusted under 35 U.S.C. 154(b) by 13 days.

(21) Appl. No.: 15/017,447

(22) Filed: Feb. 5, 2016

(65) Prior Publication Data
US 2017/0228996 A1 Aug. 10, 2017

(51) Int. Cl.
*G08B 21/04* (2006.01)
*A61B 5/024* (2006.01)
*A61B 5/00* (2006.01)
*A61B 5/11* (2006.01)
*G16H 50/30* (2018.01)
*G16H 40/63* (2018.01)
*G16H 20/30* (2018.01)

(52) U.S. Cl.
CPC ...... *G08B 21/0453* (2013.01); *A61B 5/02438* (2013.01); *A61B 5/112* (2013.01); *A61B 5/486* (2013.01); *A61B 5/6803* (2013.01); *A61B 5/7275* (2013.01); *G08B 21/0438* (2013.01); *G16H 20/30* (2018.01); *G16H 40/63* (2018.01); *G16H 50/30* (2018.01); *A61B 5/1102* (2013.01); *A61B 5/742* (2013.01); *A61B 5/7405* (2013.01); *A61B 2503/10* (2013.01); *A61B 2562/0219* (2013.01)

(58) Field of Classification Search
CPC ........... G08B 21/0453; G08B 21/0438; A61B 5/486; A61B 5/742; A61B 5/02438; A61B 5/6803; A61B 5/7405; A61B 2562/0219
See application file for complete search history.

(56) References Cited

U.S. PATENT DOCUMENTS

| | | | |
|---|---|---|---|
| 1,019,592 A | 3/1912 | Booth | |
| 5,318,487 A | 6/1994 | Golen et al. | |
| 5,583,776 A | 12/1996 | Levi et al. | |
| 5,879,270 A | 5/1999 | Huish et al. | |
| 6,431,705 B1 * | 8/2002 | Linden | G02C 11/00 351/158 |
| 7,192,401 B2 | 3/2007 | Saalasti et al. | |
| 7,677,723 B2 | 3/2010 | Howell et al. | |
| 7,710,395 B2 | 5/2010 | Rogers et al. | |
| 7,764,990 B2 | 6/2010 | Martikka et al. | |
| 8,460,001 B1 | 6/2013 | Chuang | |
| 8,666,482 B2 | 3/2014 | Wegerif | |
| 8,768,445 B2 | 7/2014 | Kinnunen et al. | |
| 8,784,115 B1 | 7/2014 | Chuang | |
| 9,142,115 B2 | 9/2015 | Tao | |

(Continued)

FOREIGN PATENT DOCUMENTS

WO 2015073879 A1 5/2015

*Primary Examiner* — James J Yang
(74) *Attorney, Agent, or Firm* — Kilpatrick Townsend & Stockton LLP

(57) ABSTRACT

A method of detecting fatigue of a user during an activity includes acquiring performance data for the user during the activity and computing metrics related to the performance data. The method also includes determining that the metrics exceed a predetermined threshold, generating an alert, and communicating the alert to the user.

18 Claims, 10 Drawing Sheets

(56) References Cited

U.S. PATENT DOCUMENTS

| | | |
|---|---|---|
| 9,370,691 B2 | 6/2016 | Nissila et al. |
| 9,517,028 B1 | 12/2016 | Saalasti et al. |
| 9,595,181 B2 | 3/2017 | Katingari et al. |
| 9,665,873 B2 | 5/2017 | Ackland et al. |
| 9,693,727 B1 | 7/2017 | Saalasti et al. |
| 9,694,239 B2 | 7/2017 | Case, Jr. et al. |
| 9,771,081 B2 | 9/2017 | Grube et al. |
| 9,781,106 B1 | 10/2017 | Vitas et al. |
| 9,873,018 B2 | 1/2018 | Flaction et al. |
| 9,895,096 B2 | 2/2018 | Nims et al. |
| 9,937,381 B2 | 4/2018 | Case, Jr. et al. |
| 2001/0022828 A1 | 9/2001 | Pyles et al. |
| 2003/0144829 A1 | 7/2003 | Geatz et al. |
| 2004/0046666 A1 | 3/2004 | Yasuchi |
| 2005/0283205 A1 | 12/2005 | Lee et al. |
| 2008/0214360 A1* | 9/2008 | Stirling ............... A61B 5/1038 482/9 |
| 2009/0043531 A1* | 2/2009 | Kahn .................... G16H 40/63 702/149 |
| 2009/0082994 A1 | 3/2009 | Schuler et al. |
| 2009/0240305 A1 | 9/2009 | Lee et al. |
| 2009/0312150 A1 | 12/2009 | Wu |
| 2011/0227812 A1 | 9/2011 | Haddick et al. |
| 2011/0288381 A1 | 11/2011 | Bartholomew et al. |
| 2013/0023798 A1* | 1/2013 | Greene ............... A61B 5/6828 600/595 |
| 2013/0144181 A1 | 6/2013 | Fogt et al. |
| 2013/0222214 A1 | 8/2013 | Takeda et al. |
| 2014/0002239 A1 | 1/2014 | Rayner |
| 2014/0049558 A1 | 2/2014 | Kraus |
| 2014/0067096 A1* | 3/2014 | Aibara .................. A63B 71/06 700/91 |
| 2014/0180621 A1 | 6/2014 | Poduri et al. |
| 2014/0287806 A1 | 9/2014 | Balachandreswaran |
| 2014/0316305 A1* | 10/2014 | Venkatraman ........ A61B 5/1112 600/595 |
| 2015/0009121 A1 | 1/2015 | Chuang et al. |
| 2015/0120017 A1 | 4/2015 | Wisbey et al. |
| 2015/0120018 A1 | 4/2015 | Wisbey et al. |
| 2015/0127298 A1 | 5/2015 | Gangumall et al. |
| 2015/0138074 A1 | 5/2015 | Hennelly et al. |
| 2015/0145643 A1 | 5/2015 | Katingari et al. |
| 2015/0179050 A1 | 6/2015 | Katingari et al. |
| 2015/0182130 A1 | 7/2015 | Utter, II |
| 2015/0182164 A1 | 7/2015 | Utter, II |
| 2015/0186609 A1 | 7/2015 | Utter, II |
| 2015/0226577 A1 | 8/2015 | Le Grand et al. |
| 2015/0241969 A1 | 8/2015 | Elangovan et al. |
| 2015/0247729 A1 | 9/2015 | Meduna |
| 2015/0338236 A1 | 11/2015 | Hoffman et al. |
| 2016/0000373 A1 | 1/2016 | Karavirta |
| 2016/0007849 A1 | 1/2016 | Krueger |
| 2016/0022200 A1 | 1/2016 | Wisbey et al. |
| 2016/0026856 A1 | 1/2016 | Wisbey et al. |
| 2016/0027324 A1 | 1/2016 | Wisbey et al. |
| 2016/0030809 A1 | 2/2016 | Wisbey et al. |
| 2016/0058372 A1 | 3/2016 | Raghuram et al. |
| 2016/0103002 A1 | 4/2016 | Milota |
| 2016/0058356 A1 | 5/2016 | Jayaraman et al. |
| 2016/0178392 A1 | 6/2016 | Goldfain |
| 2016/0196758 A1 | 7/2016 | Causevic |
| 2016/0338636 A1 | 11/2016 | Idrees et al. |
| 2016/0341579 A1 | 11/2016 | Kimura et al. |
| 2016/0353995 A1 | 12/2016 | Oleson et al. |
| 2017/0049334 A1 | 2/2017 | Saalasti et al. |
| 2017/0067933 A1 | 3/2017 | Miller et al. |
| 2017/0069188 A1 | 3/2017 | Addison et al. |
| 2017/0127957 A1 | 5/2017 | Wisbey et al. |
| 2017/0153121 A1 | 6/2017 | Hsu |
| 2017/0188894 A1 | 7/2017 | Chang et al. |
| 2017/0189752 A1 | 7/2017 | Mohrman et al. |
| 2017/0227374 A1 | 8/2017 | Theytaz et al. |
| 2017/0227375 A1 | 8/2017 | Parkh et al. |
| 2017/0227571 A1 | 8/2017 | Theytaz et al. |
| 2017/0266496 A1 | 9/2017 | Case, Jr. et al. |
| 2018/0043211 A1 | 2/2018 | Mohrman et al. |

* cited by examiner

METHOD AND SYSTEM FOR DETECTING FATIGUE IN AN ATHLETE

CROSS-REFERENCE TO RELATED APPLICATIONS

The following regular U.S. patent applications (including this one) are being filed concurrently, and the entire disclosure of the other application is incorporated by reference into this application for all purposes:

application Ser. No. 15/017,390, filed Feb. 5, 2016, entitled "METHOD AND SYSTEM FOR CALIBRATING A PEDOMETER";
application Ser. No. 15/017,401, filed Feb. 5, 2016, entitled "METHOD AND SYSTEM FOR CALIBRATING A PEDOMETER", issued as U.S. Pat. No. 10,197,592 on Feb. 5, 2019;
application Ser. No. 15/017,413, filed Feb. 5, 2016, entitled "METHOD AND SYSTEM FOR CALIBRATING A PEDOMETER";
application Ser. No. 15/017,420, filed Feb. 5, 2016, entitled "METHOD AND SYSTEM FOR CALIBRATING A PEDOMETER"; and
application Ser. No. 15/017,437, filed Feb. 5, 2016, entitled "METHOD AND SYSTEM FOR CALIBRATING A PEDOMETER".

BACKGROUND OF THE INVENTION

Sport activities such as jogging, biking, and the like are often performed in conjunction with a device that displays sport-related data, for example, heart pulse, speed, pace, calories burned, and the like. Such sport-related data can be displayed to the person participating in the sport activities using sports equipment.

Despite the progress made in the area of sports equipment, there is a need in the art for improved methods and systems related to sports equipment. In particular, there is a need in the art for methods and systems that provide for detection of the fatigue level of an athlete and an early indication of an increase in the fatigue level of the athlete.

SUMMARY OF THE INVENTION

The present invention relates generally to electronic devices. More particularly, embodiments of the present invention provide methods and systems for detecting an athlete's movements, in particular a method for detecting a runner's fatigue level. Using embodiments of the present invention, for example, implemented using a head-mounted display (e.g., sport glasses), the athlete is provided with early detection warnings related to an increase in the fatigue level so that the athlete can modify their activity to slow down, stop running, or modify the running technique, thereby improving their performance and training efficiency as well as safeguarding them from injuries.

The inventors have determined that many amateur athletes, whether they are beginners or more experienced, do not always know with enough precision the most energetically efficient movements that should be performed when running or how to improve their performance in the most advantageous manner. In particular, they cannot always promptly recognize when they are running under conditions that may be dangerous for their body, thus being at risk of experiencing physical strain, physiological distress, or exhaustion. Moreover, runners often fail to manage their physical resources properly during sustained effort. If a runner exercises too vigorously, the energy source switches from lipids to glucose stored in the muscles, which are of limited quantity and are consumed very quickly. Once lipids and glucose run out, the athlete "crashes" under exhaustion.

Runners are often not able to identify the early signs of an increasing level of fatigue, and, therefore, they can put their body at risk and fail to properly ration their energy during an activity and successfully complete their exercise routine. Therefore, embodiments of the present invention address these issues using, in one embodiment, a head-mounted pedometer. The present invention is not limited to head-mounted pedometers, but is also applicable in a variety of activity monitoring applications.

According to an embodiment of the present invention, a method of detecting fatigue of a user during an activity is provided. The method includes acquiring performance data for the user during the activity and computing metrics related to the performance data. The method also includes determining that the metrics exceed a predetermined threshold, generating an alert, and communicating the alert to the user.

According to another embodiment of the present invention, a method of alerting a user of fatigue during exercise is provided. The method includes a) acquiring a heart rate signal for the user during the exercise, b) acquiring a speed signal for the user during the exercise, and c) determining a slope of terrain in a vicinity of the user. The method also includes d) computing a heart rate to speed ratio for the user during the exercise, e) comparing the heart rate to speed ratio to a predetermined threshold, and f) iterating elements a) through e) until the heart rate to speed ratio is greater than the predetermined threshold. The method further includes g) generating an alert to the user based, at least in part, on the heart rate to speed ratio being greater than the predetermined threshold. The heart rate to speed ratio for the user can be associated with the slope of terrain in the vicinity of the user. For example, the predetermined threshold can be a function of the slope of the terrain in the vicinity of the user.

According to yet another embodiment of the present invention, a method of alerting a user of fatigue during exercise is provided. The method includes a) acquiring a speed signal for the user during the exercise, b) determining a slope of terrain in a vicinity of the user, and c) acquiring contact time and step cycle time using an accelerometer. The method also includes d) computing a step cycle time and a variability of the step cycle time, e) comparing the variability of the step cycle time to a predetermined threshold, and f) generating an alert to the user if the variability of the step cycle time is greater than the predetermined threshold. The method further includes g) iterating elements a) through f) until the variability of the step cycle time is greater than the predetermined threshold. The accelerometer can be a component of an inertial motion unit included in a wearable electronic device. As examples, the inertial motion unit can include a barometer and/or a gyroscope.

According to a specific embodiment of the present invention, a method of alerting a user to fatigue during exercise is provided. The method includes a) acquiring a heart rate signal during the exercise, b) computing a plurality of heart rate periods and statistical measures for the plurality of heart rate periods, and c) computing a variation of the statistical measures for the plurality of heart rate periods. The method also includes d) comparing the variation of the statistical measures to a predetermined threshold and e) iterating elements a) through d) until the variation of the statistical measures is greater than the predetermined threshold. The method further includes f) generating an alert to the user once the variation of the statistical measures is greater than the predetermined threshold.

According to another specific embodiment of the present invention, a method of alerting a user to instantaneous fatigue during interval training is provided. The method includes a) acquiring a first heart rate signal after a high intensity period of the interval training and b) acquiring a second heart rate signal after a low intensity period of the interval training. The method also includes c) determining if a decrease in heart rate between the first heart rate signal and the second heart rate signal is less than or equal to a predetermined threshold and d) generating an alert to the user if the decrease in heart rate is less than or equal to the predetermined threshold. In performing this methods, the user can utilize an inertial motion unit included in a wearable device to collect the heart rate signals and other information. In one embodiment, the method can also include determining that the high intensity period of the interval training and the low intensity period of the interval training were performed on substantially level terrain.

According to yet another specific embodiment of the present invention, a method of alerting a user to accumulated fatigue after interval training is provided. The method includes acquiring a first heart rate signal at a first time following a last high intensity period of the interval training and acquiring a second heart rate signal at a second time after the first time. The method also includes acquiring a third heart rate signal at a third time after the second time and determining that differences between at least the first heart rate signal, the second heart rate signal, and the third heart rate signal are less than or equal to a set of predetermined thresholds. The method further includes generating an alert to the user to indicate accumulated fatigue. The alert can include a visual signal from a display or a sound or a vibration.

Numerous benefits are achieved by way of the present invention over conventional techniques. For example, embodiments of the present invention provide methods and systems to measure fatigue based on physiological factors including heart rate and stride variation. Embodiments of the present invention help users avoid "over exercising," which can occur with amateur athletes, who tend to exercise too hard or for too long. Because managing the user's physical resources is one of the greatest challenges when running, the ability to maintain a consistent pace is crucial in endurance sports, embodiments provide a "safety net" of sorts by preventing mistakes and protecting the user from danger, for instance, body shutdown, thereby helping the athlete plan from session to session by monitoring their physical attributes. These and other embodiments of the invention along with many of its advantages and features are described in more detail in conjunction with the text below and attached figures.

DETAILED DESCRIPTION OF SPECIFIC EMBODIMENTS

Embodiments of the present invention relate generally to electronic devices. More particularly, embodiments of the present invention provide methods and systems for detecting an athlete's movements, in particular a method for detecting a runner's fatigue level. Using embodiments of the present invention, for example, implemented using a head-mounted display (e.g., sport glasses), the athlete is provided with early detection warnings related to an increase in the fatigue level so that the athlete can modify their activity to slow down, stop running, or modify the running technique, thereby improving their performance and training efficiency as well as safeguarding them from injuries.

Figure 1:
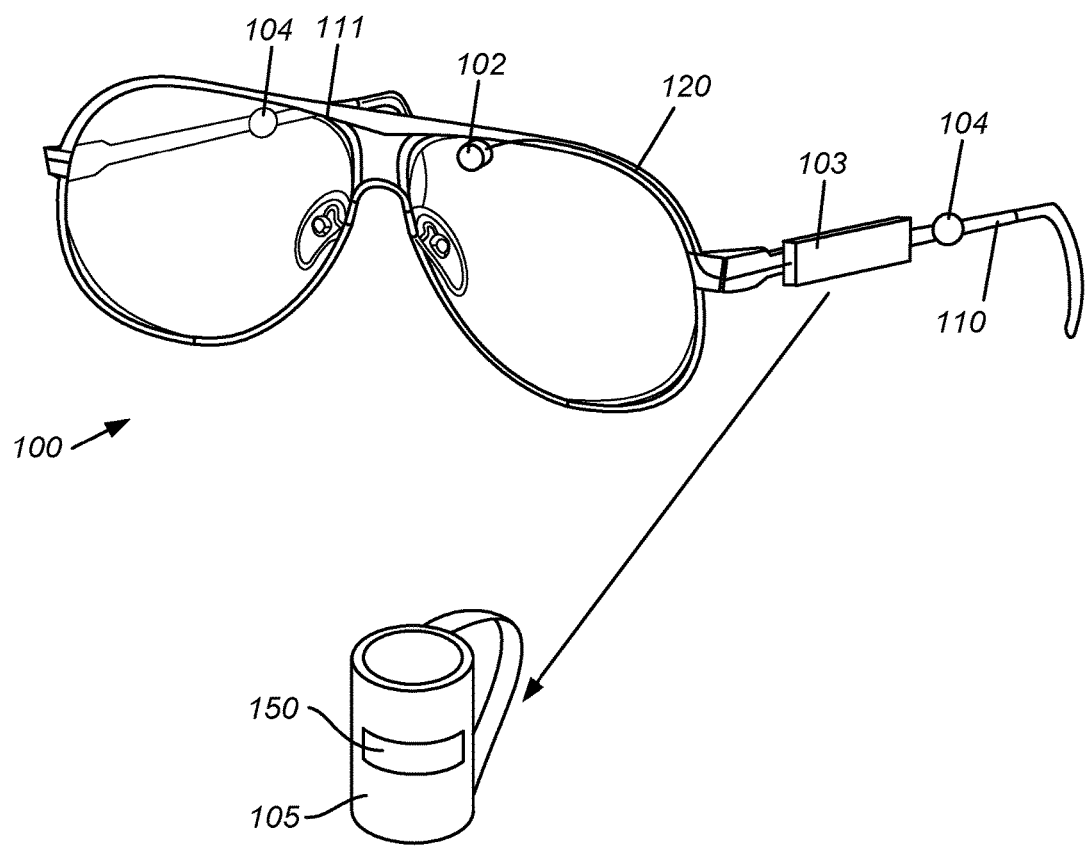
FIG. 1 shows a perspective view of a head-mounted device according to an embodiment of the present invention.
Figure 2:
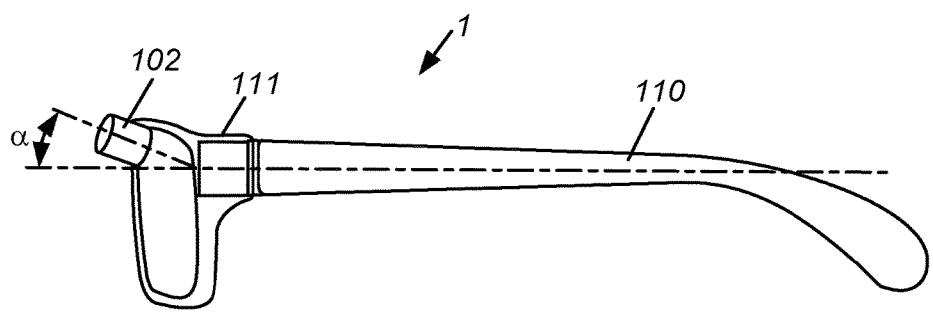
FIG. 2 shows a side view of the projection component of the head-mounted device illustrated in FIG. 1.

FIG. 1 shows a perspective view of a head-mounted device according to an embodiment of the present invention. FIG. 2 shows a side view of the projection component of the head-mounted device illustrated in FIG. 1. As illustrated in FIGS. 1 and 2, the head-mounted device includes a head-mounted display (e.g., in the form of glasses with an integrated display) that can be, in one embodiment, a non-see-through retinal projection device performing a direct image projection into an user's eye. Alternatively, the device 102 can be a LCD or a different device arranged to perform an indirect projection of an image. In the following description, reference will be made to a retinal projection device, but the invention applies to any kind of head-mounted display.

The head-mounted electronic device 100 (e.g., in the form of sport glasses) illustrated in FIGS. 1 and 2 includes a micro-projection component 102, a control component 103 and an optional remote control 105. The micro-projection component 102 and the control component 103 are mounted onto existing glasses in the illustrated embodiment, but could be integral with dedicated glasses or goggles. The micro-projection component 102 can be connected with the control component 103 over a wired connection 120. Alternatively, those two components 102 and 103 can be integrated as one single part. Alternately, a wireless connection can be used. The remote control 105 can be integrated in to the head-mounted electronic device 100 in some embodiments. The processor in the control component is operable to acquire a heart beat rate signal from a set of sensors 104 arranged to measure the heart beat rate at the user's temple.

In other embodiments, a sensor on the bridge measures heart rate by contact with the user's nose.

The control component can include a processor that can receive data from and send data to the various components of the head-mounted electronic device 100, for example, the sensors 104.

The remote control 105 can be either included in the head-mounted electronic device 100 or mounted onto different sport equipment, for example on a ski or walking pole, on a bicycle handlebar, or on a scuba or diving equipment. It could also be integral with one such dedicated sport equipment. Alternatively, it could be worn on a finger, for example as a ring on the forefinger or other finger. The remote control may comprises haptic means 150, such as at least one roller and/or at least or one button or a tactile surface, that can be manipulated with the user's thumb or fingers for entering command, such as indication selection commands and indication confirmation commands, that are wirelessly transmitted to a receiver part of the control component 103. The wireless connection can be based for example on a Bluetooth, Ant, Zigbee or a proprietary protocol. The remote control can include a battery. Alternatively, the remote control could be powered by an energy harvesting system, for example using a microgenerator for producing power from movements of the remote control, or using solar energy.

The remote control 105 can be used, as cited above, for activating the micro-projection component 102 (i.e., activating the display of information related to the sport activity) due to a user action. Alternatively, the micro-projection component 102 can be automatically turned on by a user predefined event or threshold (for example, every kilometer, every predefined time interval or when the heart beat rate exceeds a threshold).

Therefore, the micro-projection component 102 can be triggered selectively as this control might come on demand from the user or can be generated automatically by the processor included in the head-mounted electronic device 100. The on/off state of the micro-projection component 102 does not mean the on/off state of the head-mounted electronic device 100. when the micro-projection component 102 is switched off, the head-mounted electronic device 100 continues to work in the usual manner.

The micro-projection component 102 can be permanently, removably or re-adhesively mounted onto existing glasses or goggles. In the illustrated embodiment, the micro-projection component 102 is directly mounted, for example using a permanent or re-adherable adhesive, onto the external surface of one lens of the head-mounted electronic device 100. Alternatively, the micro-projection component 102 can be mounted onto the external surface of one lens, or on a temple 110 of the glasses, or on the frame 111, using fixing means such as hook-and-loop fasteners, or clips. The user can preferably adapt the position of the micro-projection component 102 according to his viewing preferences and specific morphology.

As can be seen in particular on FIG. 2, the micro-projection component 102 is mounted onto, directly against or at short distance from the external surface of a lens of a set of glasses in this embodiment, placed, for example, at the minimum distance required to form an image in focus, whether the micro-projection component 102 sits behind or through the lens of the head-mounted electronic device 100. Preferably, the micro-projection component 102 is attached to the frame 111 of the head-mounted electronic device 100.

The micro-projection device 102 is preferably mounted above or possible below the line of sight of the user when the user views the display in a horizontal direction with the head in a neutral, straight position. The micro-projection device 102 is preferably mounted so that the middle direction of the beam light that it emits is not horizontal when the head-mounted electronic device 100 are horizontal, so as to create a vertical angle $\alpha$ between the middle projection direction and the horizontal viewing direction. In this way, the image projected by the micro-projection component 102 stays in the user's peripheral vision most of the time and therefore is not focused on by the user, unless the user moves their gaze upwards (or possibly downwards) towards the micro-projection component 102. In some embodiments, the vertical angle $\alpha$ is between 10° and 25°. It will be appreciated that these angles can be adjusted by the user and/or automatically.

Figure 3:
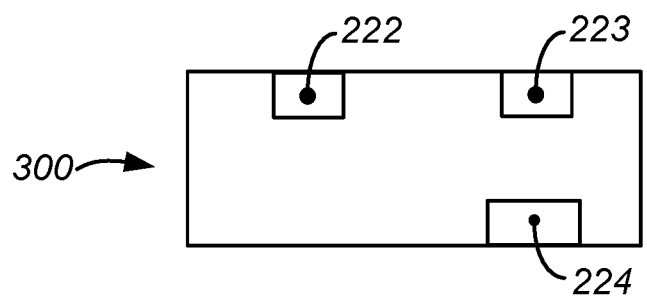
FIG. 3 is a schematic view of an inertial motion unit of the projection device according to an embodiment of the present invention.

The sensors 104 can include an inertial motion unit 200 shown in FIG. 3, which can include an accelerometer 222, a gyroscope 223, and/or a barometer 224. The barometer 224 provides data on the elevation change which can be used to determine whether the user is running uphill, downhill or on a level surface. In some embodiments, the sensors 104 may also include a GPS device or other suitable location tracking unit.

Figure 4:
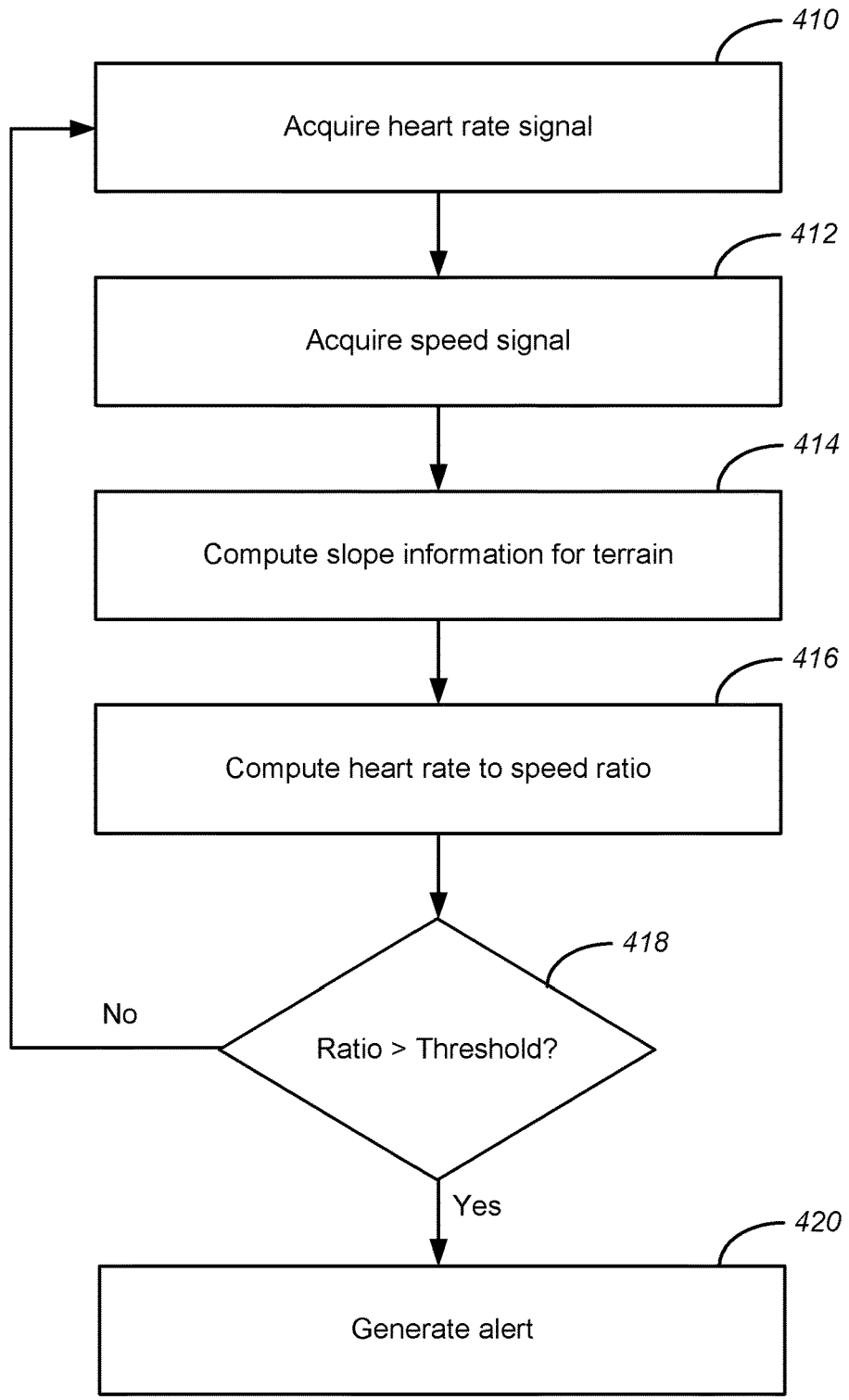
FIG. 4 is a simplified flowchart illustrating a method of detecting the fatigue of a user according to an embodiment of the present invention.

FIG. 4 is a simplified flowchart illustrating a method of detecting the fatigue of a user according to an embodiment of the invention. According to some embodiments, the heart rate of a user is correlated with speed during a calibration process. Typically, a user will run at a series of increasing speeds over level terrain, with their heart rate measured as a function of time. At each speed, a heart rate can be correlated. In some implementations, the user runs on sloped surfaces and this information is utilized to further refine the speed/heart rate correlation. The inventors have determined that during an extended training activity, the athlete's heart rate will increase over the average at a given speed, indicating an increase in fatigue. In other words, as the user's fatigue increases, the ratio of heart rate to speed increases and this increase can be used to determine the fatigue of the runner. As described in relation to FIG. 4, this increase in heart rate (e.g., increase of the heart rate to speed ratio over a predetermined threshold) can be used as an early indicator of the athlete's fatigue. As described below, embodiments of the present invention utilize contextual information (e.g., the slope of the terrain on which the athlete is running) to control for heart rate variation that does not indicate fatigue.

Referring to FIG. 4, the method of detecting the fatigue level of the user includes receiving a heart rate signal from a sensor (410), for example sensor 104 in FIG. 1. The method also includes receiving a speed signal from a sensor (412), for example, the inertial motion unit 200 that includes an accelerometer and/or a location tracking unit. As described more fully herein, the inertial motion unit and the location tracking unit can work in combination to provide speed information for the user.

The method further includes computing slope information for the current terrain (414), for example, using the atmospheric pressure sensor of the inertial motion unit. Slope information provides an indication if the user is running on surfaces that are level, uphill or downhill. Thus, the use of the term current terrain applies to the terrain in the vicinity of the user.

The heart rate to speed ratio is computed (416) using the speed signal and the heart rate signal. In some embodiments, the ratio is computed at 416 only for level path segments as determined at 414. In these embodiments, only level path segments are used, thus excluding uphill segments that would result in an increase in heart rate or a decrease in speed on account of the slope of the terrain. In other embodiments, the heart rate to speed ratio is computed (416) and compared to a threshold (e.g., the ratio computed during the calibration process) (418) on the level segments or to values associated with the current slope of the runner's path. In some embodiments, the heart rate to speed ratio that is computed for the user is associated with the slope of terrain in the vicinity of the user. As a result, the thresholds can vary depending on the slope of the terrain, with lower thresholds for level terrain and higher thresholds for steeper terrain.

Referring to 418 of FIG. 4, the ratio of the heart rate to speed, which can be referred to as a fatigue value, is compared to a threshold value. If the ratio is greater than the threshold value, an alarm message can be provided to the user. As an example, the alarm or alert can be displayed using the micro-projection component 102. Alternatively, the alarm message can be a sound, a vibration, or the like. Preferably, the threshold value is obtained by combining historical data combined with a fixed value defined experimentally. The historical data can be ratio values calculated as described above in a time period before the one during which the fatigue level has to be determined, for example, at the beginning of a running session or at a previous time. In some embodiments, levels of fatigue are determined by comparison of the ratio to a set of threshold levels, with lower thresholds associated with lower levels of fatigue and higher thresholds associated with higher levels of fatigue. One of ordinary skill in the art would recognize many variations, modifications, and alternatives.

If the ratio of the heart rate to speed is less than or equal to the threshold, then the method continues at 410 by acquiring heart rate and speed signals at subsequent times (410/412). Thus, the method iterates until either the user experiences fatigue measured by the ratio exceeding the threshold or the user stops the activity.

It should be appreciated that the specific steps illustrated in FIG. 4 provide a particular method of detecting the fatigue of a user according to an embodiment of the present invention. Other sequences of steps may also be performed according to alternative embodiments. For example, alternative embodiments of the present invention may perform the steps outlined above in a different order. Moreover, the individual steps illustrated in FIG. 4 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 5:
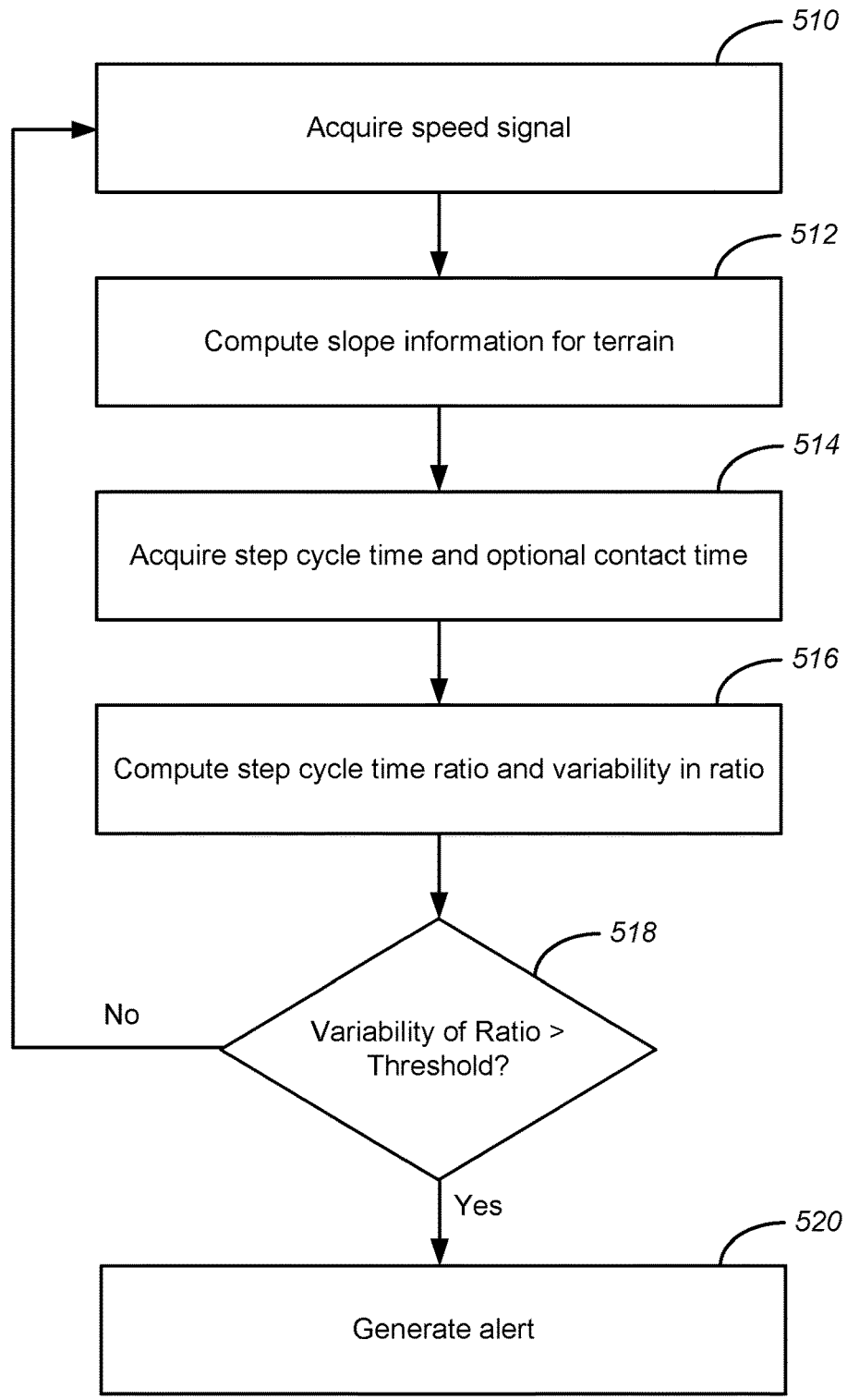
FIG. 5 is a simplified flowchart illustrating a method of detecting fatigue of a user based on cadence variability according to an embodiment of the present invention.
Figure 11:
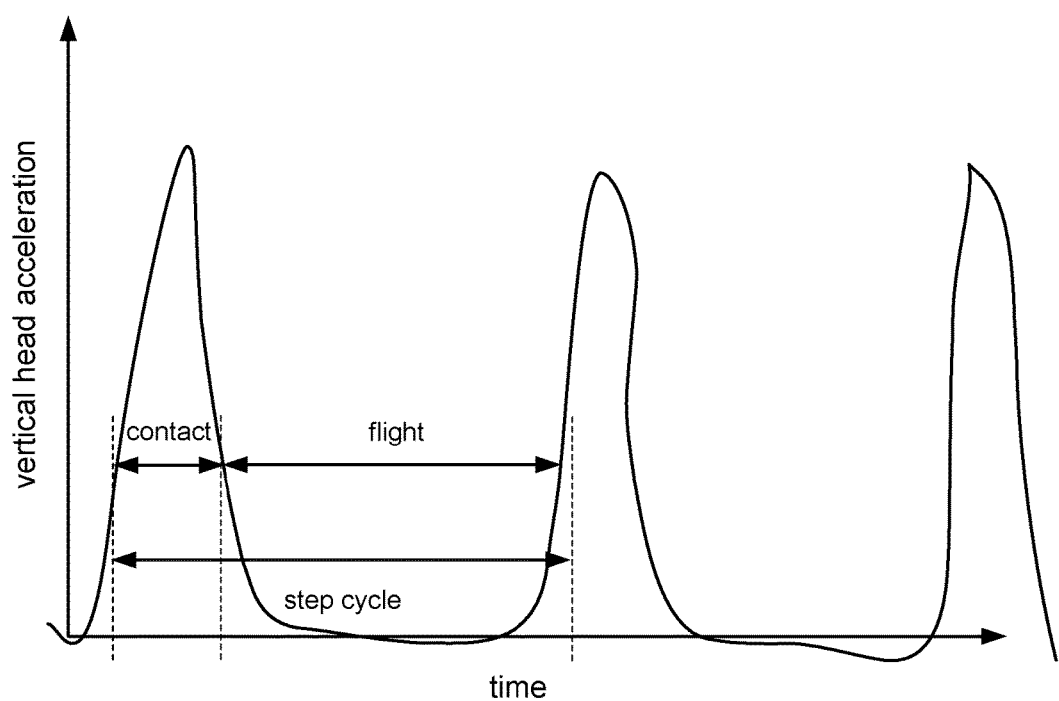
FIG. 11 is a plot illustrating vertical head acceleration as a function of time according to an embodiment of the present invention.

FIG. 5 is a simplified flowchart illustrating a method of detecting fatigue of a user based on cadence variability according to an embodiment of the present invention. In this method, the accelerometer of the inertial motion unit is used to measure the vertical acceleration of the runner's head and to calculate various metrics associated therewith, including the runner's step cycle time, also referred to as gait cycle time, which is the time between adjacent contact events. In some embodiments, contact time, which is the length of time during which the runner's foot is in contact with the ground during a step and/or flight time, which is the length of time during which the runner's foot is not in contact with the ground. FIG. 11 is a plot illustrating vertical head acceleration as a function of time according to an embodiment of the present invention. As illustrated in FIG. 11, the acceleration profile can be characterized by several parameters including contact time, flight time, and the step cycle time. Depending on the speed of the runner, the contact time varies, with fast contact times for sprinting and longer contact times for jogging.

When a runner is not fatigued, the step cycle time is substantially constant. However, as the runner fatigues, the step cycle time begins to become variable and can be used as an early measure of fatigue. Although different runners may have differing cadence and differing contact times and step cycle times, the metrics are unique to a user. As the runner fatigues, the step cycle time experiences a variability as described below, enabling this method of fatigue detection, even before, for some people, the increase in the heart rate to speed ratio discussed in relation to FIG. 4 is useful.

Referring to FIG. 5, the method includes receiving a speed signal from a sensor (510), for example, the inertial motion unit 200 that includes an accelerometer and/or the location tracking unit. The method also includes computing slope information for the current terrain (512), for example, using the atmospheric pressure sensor of the inertial motion unit. Slope information provides an indication if the user is running on surfaces that are level, uphill or downhill. The method further includes determining the step cycle time (and/or an optional contact time) for the user's stride (514), for example, for a set of adjacent steps. In some embodiments, the contact time and the step cycle time for each step are determined and a running set of contact times and step cycle times are obtained, whereas in other embodiments, averaging of a number of contact time and step cycle time measurements is used to smooth the computed data.

The step cycle time and the variability in the step cycle time are computed (516). In some embodiments, terrain with a level slope is utilized so that the step cycle time is only used when the user is running on a level surface, thus excluding uphill and downhill segments. In other embodiments, step cycle time associated when different slopes are utilized as will be evident to one of skill in the art. The variability, which can also be referred to as the variance, can be computed as the standard deviation of the step cycle time (e.g., over a predetermined number of samples, for instance, 20 samples) divided by the mean of the step cycle time (e.g., computed over the predetermined number of samples). For a person with a consistent stride (e.g., an unfatigued person), the variability is zero because the standard deviation is zero, independent of the speed. In some embodiments, the contact time and/or flight time is computed and similar calculations are performed to determine the contact time/flight time and the variability in the contact time/flight time. One of ordinary skill in the art would recognize many variations, modifications, and alternatives.

The inventors have determined that the variability (i.e., the standard deviation divided by the mean) of the step cycle time will stay constant as the user's speed increases or decreases and, as a result, variation in the ratio of the standard deviation to the mean of the step cycle time can indicate fatigue in the runner. The variability in the step cycle time is compared to a threshold (518) and if the variability exceeds the threshold, then an alarm message can be provided to the user, for example, through the micro-projection component 102, another suitable display, or the like. Alternatively, the alarm message can be a sound, a vibration, or the like.

In some embodiments, levels of fatigue are determined by comparison of the variability in the step cycle time to a set of threshold levels, with lower thresholds associated with lower levels of fatigue and higher thresholds associated with higher levels of fatigue. One of ordinary skill in the art would recognize many variations, modifications, and alternatives.

In some alternative embodiments, the flight time ratio or contact time ratio, equal to the flight time/contact time divided by the step cycle time and the variation in the flight time/contact time ratio are utilized to detect user fatigue. Thus, embodiments are not limited to the step cycle time, but can utilize other metrics based on the user's stride data, including contact time ratio and flight time ratio. Thus, embodiments can utilize a metric based on an analysis of the vertical acceleration of the head, for example, the variability of the step cycle time over a predefined number of steps (e.g., 20 steps). In this method, the variability of the time between two contacts with the ground for both left and right feet is used to provide an early indication of fatigue.

If the variability in the ratio is less than or equal to the threshold, then the method iterates to 510 and additional data is collected as the activity progresses. In the illustrated embodiment, the iteration loop continues until the variability exceeds the threshold, indicating fatigue, or the activity is completed.

It should be appreciated that the specific steps illustrated in FIG. 5 provide a particular method of detecting fatigue of a user based on cadence variability according to an embodiment of the present invention. Other sequences of steps may also be performed according to alternative embodiments. For example, alternative embodiments of the present invention may perform the steps outlined above in a different order. Moreover, the individual steps illustrated in FIG. 5 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 7:
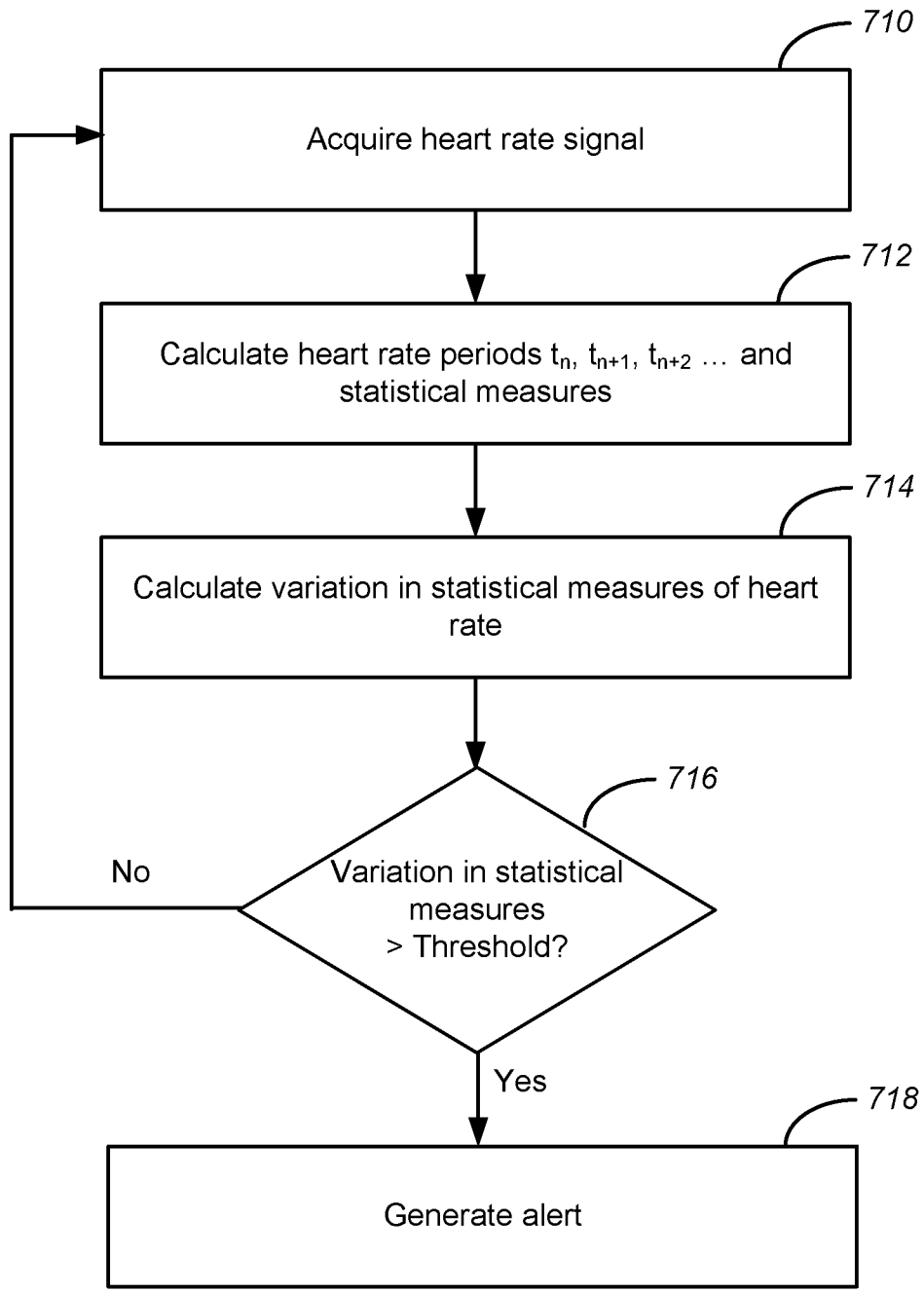
FIG. 7 is a simplified flowchart illustrating a method of detecting fatigue based on heart rate variability according to an embodiment of the present invention.

FIG. 7 is a simplified flowchart illustrating a method of detecting fatigue based on heart rate variability according to an embodiment of the present invention. The method discussed in relation to FIG. 7 utilizes the physiological result determined by the inventors that variation in the athlete's heart rate as a function of time is an indicator of fatigue.

Figure 6:
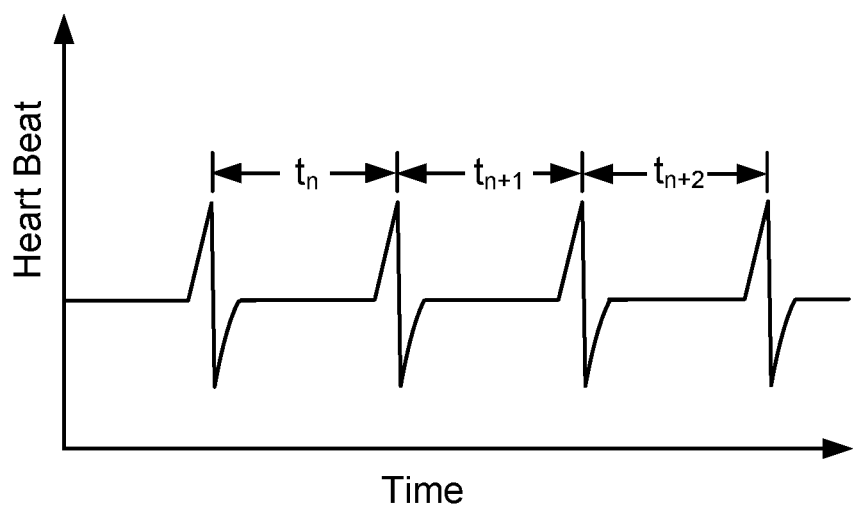
FIG. 6 is a plot of heart rate vs. time for a runner according to an embodiment of the present invention.

Referring to FIG. 7, the method includes receiving a heart rate signal from a sensor (710), for example sensor 104 in FIG. 1. The heart rate period as a function of time is recorded to provide heart rate periods $t_n$, $t_{n-1}$, $t_{n+2}$, . . . (712). FIG. 6 is a plot of heart rate vs. time for a runner according to an embodiment of the present invention. As illustrated in FIG. 6, the heart rate periods $t_n$, $t_{n+1}$, and $t_{n+2}$ are measured and recorded. Given the heart rate periods, the standard deviation and the mean of the heart rate period can be computed. The standard deviation of the heart rate period and the mean of the heart rate period can be measured over a predetermined number of periods, for example, 20 periods. The ratio of the standard deviation of the heart rate period to the mean of the heart rate period over a predefined number of periods can be computed and referred to as a fatigue ratio.

The variability of the heart rate period, represented by the fatigue ratio (i.e., the ratio of the standard deviation of the heart rate period to the mean of the heart rate period) over a predefined number of periods is determined (714). The variability is then compared to a threshold value (716). If the variability of the heart rate period, i.e., the ratio of the standard deviation of the heart rate period to the mean of the heart rate period (i.e., the fatigue ratio) exceeds the threshold, then an alarm message is provided to the user indicating an increase in fatigue over a predetermined level. The alarm or alert can be visual. Alternatively, the alarm message can be a sound or a vibration, or a combination of visual and audio elements. If the variability is less than or equal to the threshold, then the method continues to 710 and the method iterates until either fatigue is indicated or the activity is stopped. As discussed above, levels of fatigue can be detected using a set of thresholds in 716.

In comparison with wrist-mounted pulse measurement devices, embodiments of the present invention, because they are mounted on the head provide a stable platform for heart rate measurement. Blood flow in the wrist can be impacted by swinging of the arms during running and head-mounted devices do not experience this adverse effect. As a result, embodiments of the present invention are able to extract clean signals with high signal to noise ratios.

It should be appreciated that the specific steps illustrated in FIG. 7 provide a particular method of detecting fatigue based on heart rate variability according to an embodiment of the present invention. Other sequences of steps may also be performed according to alternative embodiments. For example, alternative embodiments of the present invention may perform the steps outlined above in a different order. Moreover, the individual steps illustrated in FIG. 7 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 9:
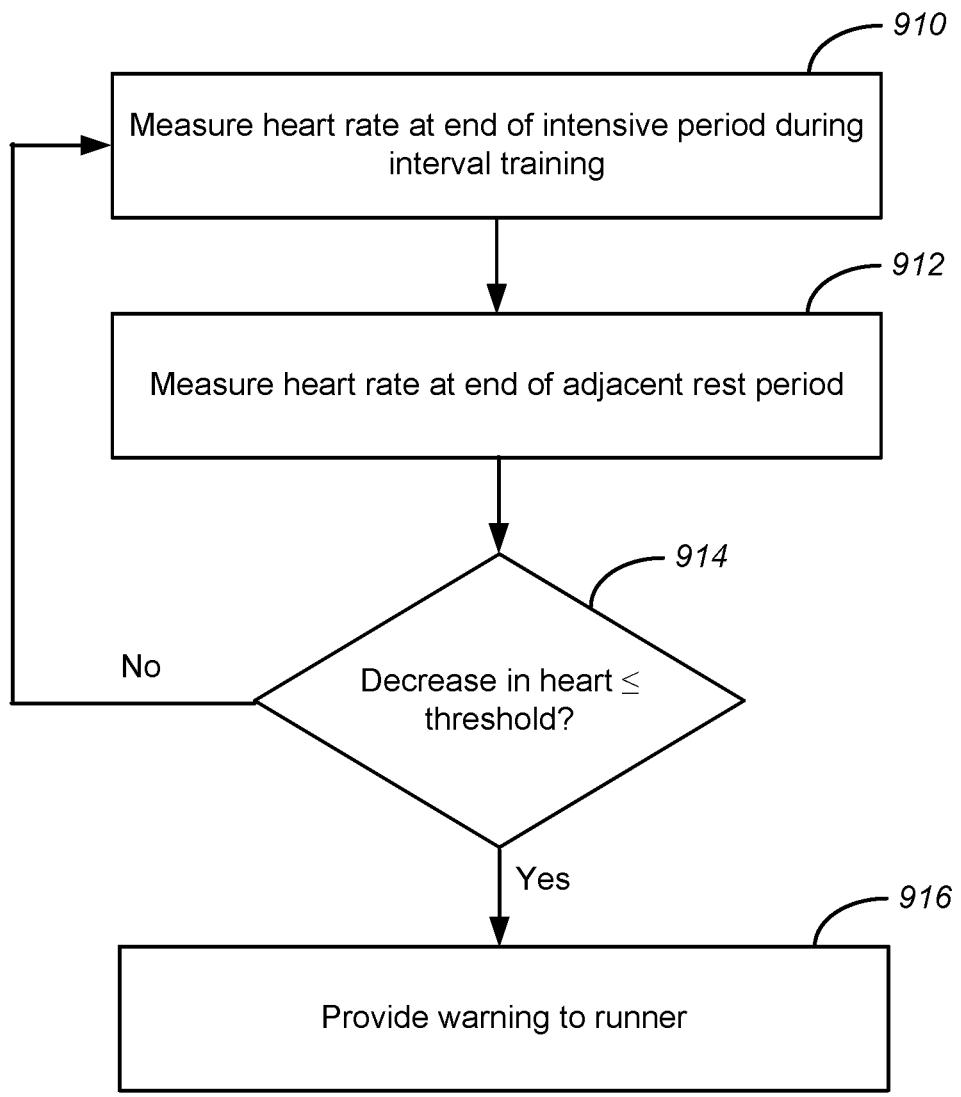
FIG. 9 is a simplified flowchart illustrating a method of detecting fatigue during interval training according to an embodiment of the present invention.
Figure 10:
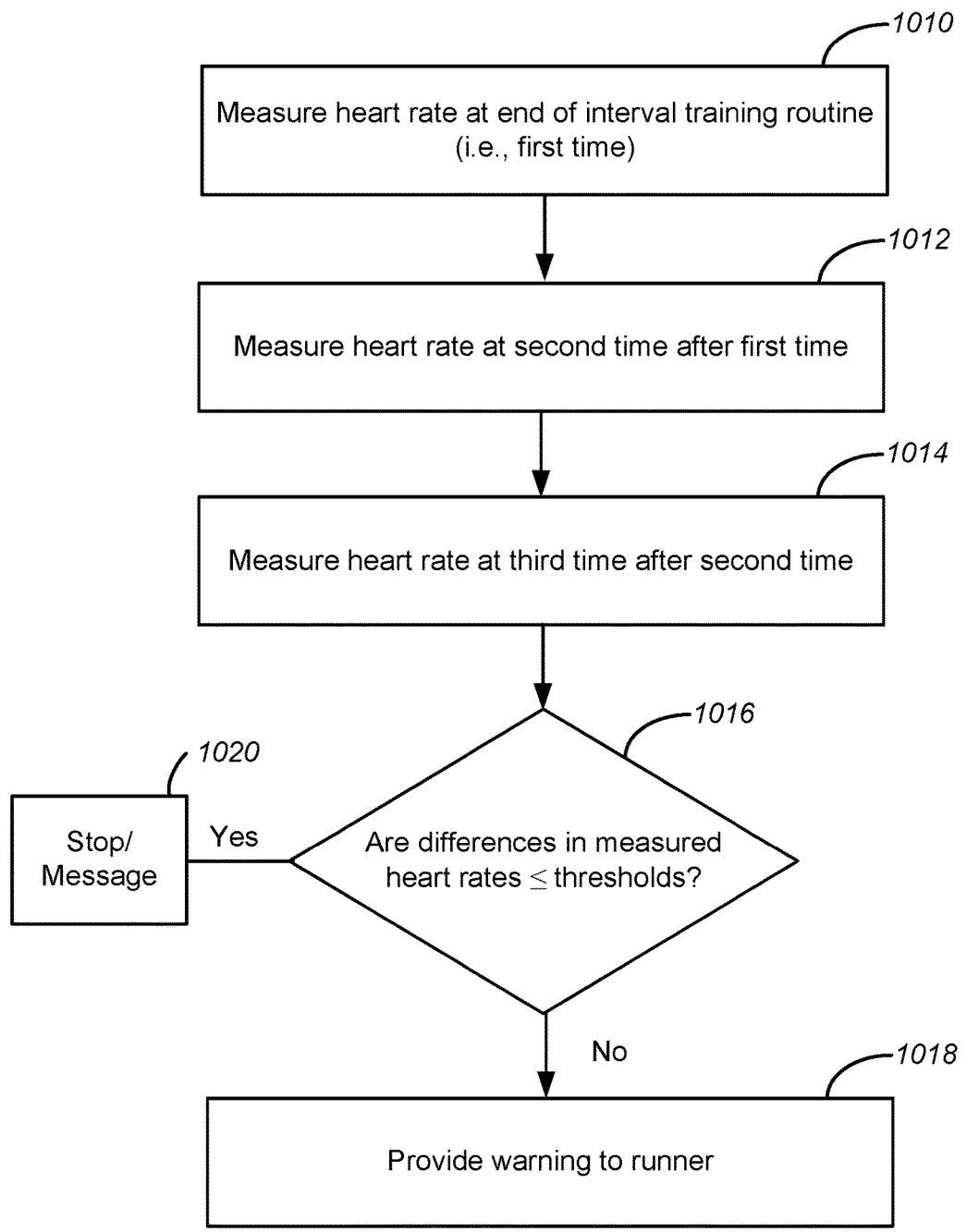
FIG. 10 is a simplified flowchart illustrating a method of detecting fatigue during interval training according to another embodiment of the present invention.

Referring to FIGS. 9 and 10, the methods described herein include monitoring fatigue at two levels: instantaneous fatigue and accumulated fatigue. Instantaneous fatigue is the fatigue characterized by the heart rate of the runner not dropping enough between intervals. Accumulated fatigue is the fatigue characterized by the heart rate of the runner not dropping quickly enough after the completion of the interval training.

FIG. 9 is a simplified flowchart illustrating a method of detecting fatigue during interval training according to an embodiment of the present invention. As illustrated in FIG. 9, the fatigue level of the user can be detected during interval training by monitoring the rate at which the heart rate decreases after the high intensity portion of an interval. During interval training, the runner purposely varies their speed for short periods of time. The method illustrated in FIG. 9 can be considered as a method of measuring an instantaneous fatigue level.

Figure 8:
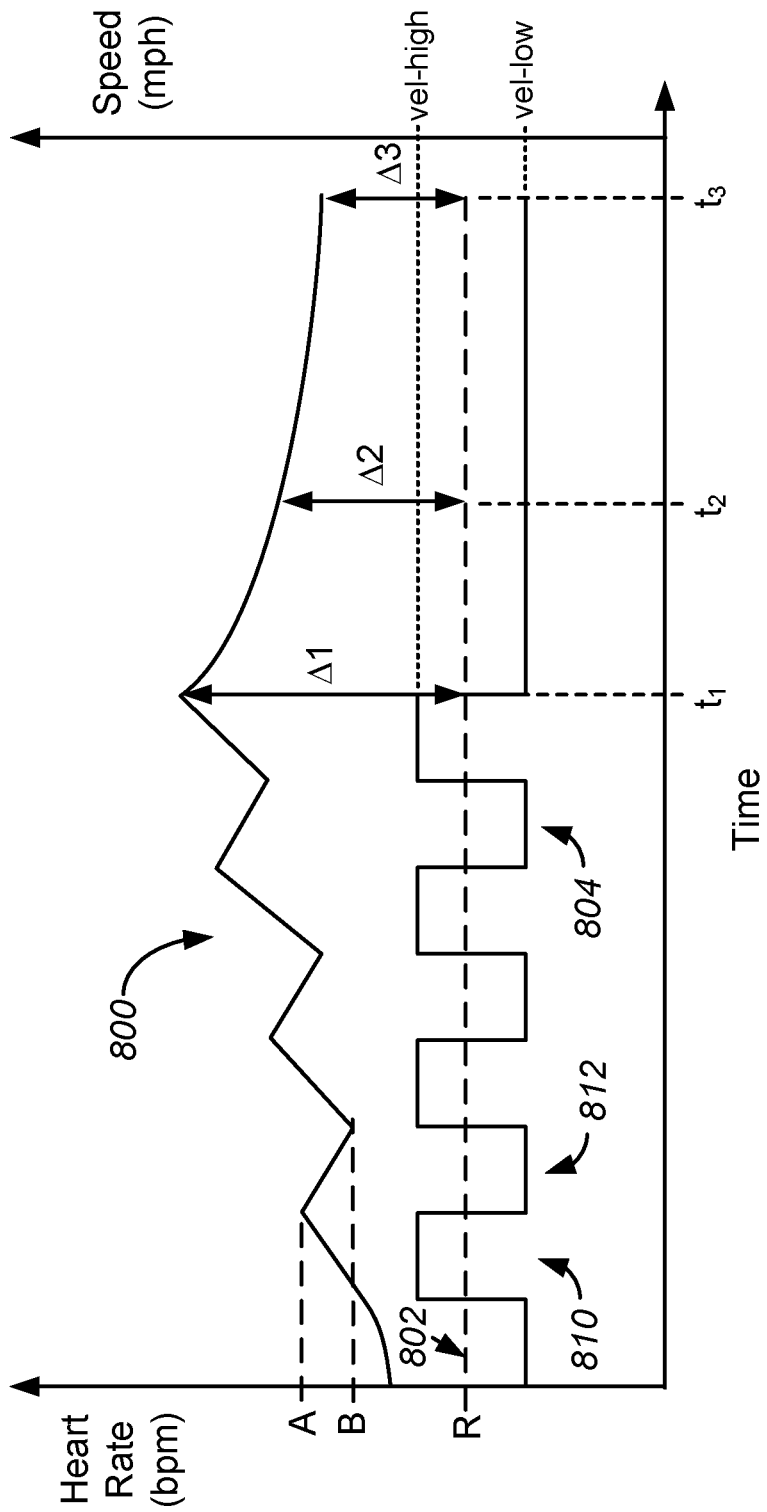
FIG. 8 is a plot illustrating the variation of the heart rate signal and the speed signal of the runner over time during interval training.

FIG. 8 is a plot illustrating the variation of the heart rate signal and the speed signal of the runner over time during interval training. In FIG. 8, the resting heart rate is indicated by curve 802 (Resting Heart Rate R). The speed of the runner is indicated by curve 804. As shown by curve 804, the speed of the runner increases from a first speed vel-low to speed vel-high during the low intensity and high intensity portions of the interval training. Curve 800 represents the runner's heart rate as a function of time during the interval training. In response to the variation of speed, the heart rate of the runner will oscillate during intensive (vel-high) and rest (vel-low) periods. The inventors have determined that the longer the runner runs, the more time the heart takes to decrease the heart rate during the period of time at which the runner is at the low intensity speed vel-low, which is an indication of the fatigue of the runner.

The method includes, during interval training, measuring the heart rate of the runner at the end of an intensive period (910) and measuring the heart rate of the runner the end of an adjacent rest or low intensity period (912). As illustrated in FIG. 8, after intensive period 810, the heart rate decreases from level A to level B by the end of the rest period 812. A determination is made if the decrease in heart rate during the rest period is less than or equal to a predetermined threshold (914). In an embodiment, the predetermined threshold is a percentage of either the heart rate at the end of the intensive period, the heart rate at the end of the rest period, or a value computed based on these heart rates such as an average. As an example, the predetermined threshold could be 10% of the heart rate at the end of the intensive period. The predetermined threshold can be modified to be different for each user. If the decrease is greater than the predetermined threshold, then the method continues to the next intensive/rest period pair at 910/912

If the decrease is less than or equal to the predetermined threshold, then a warning, alarm, or alert can be generated and delivered to the user (916). If the decrease is not less than or equal to the threshold, then the method iterates to 910 and the heart rate is measured at the end of the next intensive period of the interval training. Although measurement of the heart rate in the rest period adjacent to and following the intensive period is illustrated in FIG. 9, this is not required by the present invention and, for example, the rest period following the intensive period after the intensive period that was measured in 910 can be utilized to gauge the runner's fatigue level. One of ordinary skill in the art would recognize many variations, modifications, and alternatives.

It should be noted that as the athlete improves their level of fitness, the number of intervals performed before the athlete reaches the point at which the heart rate decrease is less than or equal to the threshold can increase as fitness increases. In some embodiments, as the number of intervals increases, the athlete is able to modify the threshold values to further improve the quality of their training routines.

It should be appreciated that the specific steps illustrated in FIG. 9 provide a particular method of detecting fatigue during interval training according to an embodiment of the present invention. Other sequences of steps may also be performed according to alternative embodiments. For example, alternative embodiments of the present invention may perform the steps outlined above in a different order. Moreover, the individual steps illustrated in FIG. 9 may include multiple sub-steps that may be performed in various sequences as appropriate to the individual step. Furthermore, additional steps may be added or removed depending on the particular applications. One of ordinary skill in the art would recognize many variations, modifications, and alternatives.

FIG. 10 is a simplified flowchart illustrating a method of detecting fatigue during interval training according to another embodiment of the present invention. The method illustrated in FIG. 10 can be considered as a method of measuring an accumulated fatigue level.

The method includes measuring the heart rate of the runner at the end of the interval training routine (1010). Referring to FIG. 8, at time $t_1$, which can be referred to as a first time, the runner's heart rate is measured as the interval training ends at a heart rate that is Δ1 beats per minute higher than the resting heart rate R. The method also includes measuring the heart rate of the runner at a second time $t_2$ later than the first time $t_1$ (1012). As illustrated in FIG. 8, the heart rate at the second time t2 is Δ2 beats per minute higher than the resting heart rate. Then, at a third time $t_3$ later than the second time $t_2$, the runner's heart rate is measured (i.e., Δ3) (1014). As an example, the second time $t_2$ could be one minute after the end of the interval training routine and the third time $t_3$ could be three minutes after time $t_1$.

The measured heart rate values are used in a comparison with threshold values to determine if differences between the measured values are less than or equal to the threshold values (1016). As an example, if the difference between Δ1 and Δ2 is greater than a first threshold or the difference between Δ1 and Δ3 is greater than a second threshold, then the runner is experiencing accumulated fatigue and a warning message, alert, or alarm is provided to the user (1018) to warn the user/runner, for example, that they should delay their next interval training routine. For a runner who performs interval training several days in a row, the warning could indicate that the runner needs to stop interval training for a certain period until the accumulated fatigue decreases to a preferred level. If the differences are less than or equal to the thresholds, then the method is stopped. In an alternative embodiment, an optional message can be displayed to the user indicating that they have not reached the level of accumulated fatigue associated with the warnings. In some embodiments, a measure of the level of accumulated fatigue can be provided to the user even when the fatigue level is less than the threshold.

By using the method illustrated in FIG. 10, a user is able to monitor the accumulated fatigue after each interval training session in order to help the user take enough rest between consecutive interval training sessions and avoid overtraining. One of ordinary skill in the art would recognize many variations, modifications, and alternatives. In some embodiments, feedback from the user after the training cycle (e.g., level of difficulty of the cycle, level of exhaustion after the cycle, etc.) is used in combination with the methods described herein to set the thresholds for comparison. Accordingly, the methods can be customized to the user. Additionally, as the user improves their fitness, the thresholds can be adjusted in accordance with the improvement in the user's fitness.

It should be appreciated that the specific steps illustrated in FIG. 10 provide a particular method of detecting fatigue during interval training according to another embodiment of the present invention. Other sequences of steps may also be performed according to alternative embodiments. For example, alternative embodiments of the present invention may perform the steps outlined above in a different order. Moreover, the individual steps illustrated in FIG. 10 may include multiple sub-steps that may be performed in various sequences as appropriate to the individual step. Furthermore, additional steps may be added or removed depending on the particular applications. One of ordinary skill in the art would recognize many variations, modifications, and alternatives.

The methods that have been described herein can be combined to provide benefits and techniques not available using conventional techniques. As an example, the cadence variation measured using the methods described in relation to FIG. 5 could be combined with the interval training methods described in relation to FIG. 9 to provide an early indication that instantaneous fatigue is starting to exceed a desired level by reducing the threshold used in 914 as the variability in the cadence increases. Similar combinations using heart rate variability as discussed in relation to FIG. 7 could be utilized as well. One of ordinary skill in the art would recognize many variations, modifications, and alternatives.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method of detecting fatigue of a user during an activity with a head-mounted electronic device, the method comprising:
   acquiring step cycle time data for the user during the activity;
   computing a standard deviation of the step cycle time and a mean of the step cycle time;
   determining a variability of the step cycle time as the standard deviation of the step cycle time divided by the mean of the step cycle time during the beginning of an exercise session;
   setting a step variability fatigue threshold at a value greater than the variability determined during the beginning of an exercise session;
   monitoring the variability of the step cycle time;
   determining that the variability of the step cycle time exceeds the step variability fatigue threshold;
   generating an alert indicating fatigue due to the variability in the step cycle time exceeding the step variability fatigue threshold; and
   communicating the alert indicating fatigue to the user via at least one of a display, haptic element and a speaker mounted in the head-mounted electronic device.

2. The method of claim 1 further comprising acquiring data indicating a speed of the user, wherein the step variability fatigue threshold remains constant at different speeds of the user.

3. The method of claim 2 wherein the step variability fatigue threshold is adjusted based on historical data.

4. The method of claim 1 further comprising acquiring slope information for terrain in a vicinity of the user, wherein the step variability fatigue threshold is used for portions of the activity performed on level terrain.

5. The method of claim 1 wherein acquiring the step cycle time data comprises measuring vertical acceleration of the user's head as a function of time during at least a portion of the activity.

6. A method of alerting a user of fatigue during exercise with a head-mounted electronic device, the method comprising:
   a) acquiring a speed signal for the user during the exercise;
   b) determining a slope of terrain in a vicinity of the user;
   c) acquiring contact time and step cycle time using an accelerometer;
   d) computing a step cycle time and a variability of the step cycle time during the beginning of an exercise session, wherein the variability of the step cycle time is a standard deviation of the step cycle time divided by a mean of the step cycle time;
   setting a step variability fatigue threshold at a value greater than the variability determined during the beginning of an exercise session;
   monitoring the variability of the step cycle time;
   e) comparing the variability of the step cycle time to the step variability fatigue threshold;
   f) generating an alert indicating fatigue to the user if the variability of the step cycle time is greater than the step variability fatigue threshold, indicating fatigue due to the variability in the step cycle time exceeding the step variability fatigue threshold;
   communicating the alert indicating fatigue to the user via at least one of a display, haptic element and a speaker mounted in the head-mounted electronic device; and
   g) iterating elements a) through f) until the variability of the step cycle time is greater than the step variability fatigue threshold.

7. The method of claim 6 wherein determining the slope of the terrain comprises selecting a set of path segments that are level.

8. The method of claim 6 wherein computing the step cycle time comprises averaging a step cycle time for a series of step cycles.

9. The method of claim 1 wherein a plurality of predetermined thresholds are provided indicating different levels of fatigue, and a plurality of fatigue level alerts are provided corresponding the plurality of predetermined thresholds.

10. The method of claim 4 further comprising:
    acquiring a speed signal for the user during the exercise;
    determining a heart rate of the user;
    determining a heart rate to speed ratio;
    comparing the heart rate to speed ratio to a second predetermined threshold; and
    if the slope of the terrain is not level, generating an alert indicating fatigue if the heart rate to speed ratio is greater than the second predetermined threshold.

11. The method of claim 4 wherein the slope of the terrain is computed using data from a barometer.

12. A method of alerting a user of fatigue during exercise using a head mounted device, the method comprising:
    acquiring a speed signal for the user during the exercise;
    determining a slope of terrain in a vicinity of the user;
    acquiring a step cycle time;
    computing a step cycle time and a variability of the step cycle time during the beginning of an exercise session, wherein the variability of the step cycle time is a standard deviation of the step cycle time divided by a mean of the step cycle time;
    setting a step variability fatigue threshold at a value greater than the variability determined during the beginning of an exercise session;
    monitoring the variability of the step cycle time;
    comparing the variability of the step cycle time to the step variability fatigue threshold;
    generating an alert indicating fatigue to the user if the variability of the step cycle time is greater than the first step variability fatigue threshold and the slope of terrain is level, indicating fatigue due to the variability in the step cycle time exceeding the step variability fatigue threshold;
    determining a heart rate of the user;
    determining a heart rate to speed ratio;
    comparing the heart rate to speed ratio to a heart rate fatigue threshold;
    if the slope of the terrain is not level, generating an alert if the heart rate to speed ratio is greater than the heart rate fatigue threshold; and
    communicating the alert indicating fatigue to the user via the at least one of a display, haptic element and a speaker mounted in the head-mounted electronic device.

13. The method of claim 12 wherein the heart rate is determined from a sensor mounted to contact one of the user's nose and temple.

14. The method of claim 12 wherein the slope of the terrain is computed using data from a barometer.

15. The method of claim 12 wherein the step variability fatigue threshold remains constant at different speeds of the user.

16. The method of claim 12 wherein acquiring the step cycle time data comprises measuring vertical acceleration of the user's head as a function of time during at least a portion of the activity.

17. The method of claim 12 wherein a plurality of predetermined thresholds are provided indicating different levels of fatigue, and a plurality of fatigue level alerts are provided corresponding the plurality of predetermined thresholds.

18. A method of detecting fatigue of a user during an activity using a head-mounted electronic device, the method comprising:
- acquiring step cycle time data for the user during the activity by measuring vertical acceleration of the user's head, with an accelerometer in the head-mounted electronic device, as a function of time during at least a portion of the activity;
- determining a variability of the step cycle time during the beginning of an exercise session;
- setting a step variability fatigue threshold at a value greater than the variability determined during the beginning of an exercise session;
- monitoring the variability of the step cycle time;
- determining that the variability of the step cycle time exceeds the step variability fatigue threshold;
- generating a first alert indicating fatigue due to the variability in the step cycle time exceeding the threshold;
- communicating the first alert indicating fatigue to the user via at least one of a display, haptic element and a speaker mounted in the head-mounted electronic device;
- monitoring a heart rate of the user with a heart rate monitor mounted in the head-mounted electronic device;
- determining a heart rate signal from a heart rate monitor mounted in the head-mounted electronic device;
- determining a speed of the user based on a distance determination signal;
- determining a ratio of heart rate to speed for the beginning of an exercise session;
- setting a heart rate to speed fatigue threshold at a value greater than the ratio of heart rate to speed determined during the beginning of an exercise session;
- monitoring the heart rate to speed ratio;
- determining that the ratio of heart rate to speed exceeds the heart rate to speed fatigue threshold;
- generating a second alert indicating fatigue due to the heart rate to speed ratio exceeding the heart rate to speed fatigue threshold; and
- communicating the second alert indicating fatigue to the user via the at least one of a display, haptic element and a speaker mounted in the head-mounted electronic device.

* * * * *